United States Patent
Gardner et al.

(10) Patent No.: US 11,213,658 B2
(45) Date of Patent: *Jan. 4, 2022

(54) BALLOON CATHETER

(71) Applicant: SANFORD HEALTH, Sioux Falls, SD (US)

(72) Inventors: Bruce A. Gardner, Rochester, MN (US); Jeffery A Gardner, St. Clair, MO (US); David Allan Swanson, Palmyra, NJ (US)

(73) Assignee: Sanford Health, Sioux Falls, SD (US)

( * ) Notice: Subject to any disclaimer, the term of this patent is extended or adjusted under 35 U.S.C. 154(b) by 522 days.

This patent is subject to a terminal disclaimer.

(21) Appl. No.: 16/260,644

(22) Filed: Jan. 29, 2019

(65) Prior Publication Data

US 2019/0151628 A1    May 23, 2019

Related U.S. Application Data

(60) Continuation of application No. 14/987,464, filed on Jan. 4, 2016, now Pat. No. 10,307,573, which is a
(Continued)

(51) Int. Cl.
*A61M 25/10*    (2013.01)
*A61M 25/00*    (2006.01)
*A61M 25/04*    (2006.01)

(52) U.S. Cl.
CPC ...... *A61M 25/1011* (2013.01); *A61M 25/003* (2013.01); *A61M 25/0017* (2013.01); *A61M 25/04* (2013.01); *A61M 25/10* (2013.01); *A61M 25/1018* (2013.01); *A61M 25/1027* (2013.01); *A61M 25/10185* (2013.11);
(Continued)

(58) Field of Classification Search
CPC .. A61M 2025/0008; A61M 2025/0078; A61M 2210/1078; A61M 25/0017; A61M 25/003; A61M 25/007; A61M 25/04; A61M 25/10; A61M 25/1011; A61M 25/1018; A61M 25/10185; A61M 25/1027
See application file for complete search history.

(56) References Cited

U.S. PATENT DOCUMENTS 2,330,399 A    9/1943    Winder
2,912,981 A    11/1959   Keough
(Continued)

*Primary Examiner* — Kai H Weng
(74) *Attorney, Agent, or Firm* — McDonnell Boehnen Hulbert & Berghoff LLP

(57) ABSTRACT

A balloon catheter having an elongated catheter shaft defining a fluid drainage lumen and a balloon inflation lumen. The balloon catheter includes a fluid drainage port disposed about the distal end of the catheter shaft in fluid communication with the fluid drainage lumen, and a balloon inflation port disposed about the distal end of the catheter shaft in fluid communication with the balloon inflation lumen. A balloon portion is disposed about the distal end of the catheter shaft in fluid communication with the balloon inflation port. A release device is disposed in fluid communication with the balloon portion and the fluid drainage lumen, and includes an activating member. A tether is attached to the activating member of the release device. Tension applied to the tether activates the release device, enabling fluid flow from the balloon portion into the fluid drainage lumen and out of the body.

8 Claims, 6 Drawing Sheets

Related U.S. Application Data continuation of application No. 13/943,971, filed on Jul. 17, 2013, now Pat. No. 9,227,042, which is a division of application No. 12/562,658, filed on Sep. 18, 2009, now Pat. No. 8,500,684.

(52) U.S. Cl.
CPC ... *A61M 25/007* (2013.01); *A61M 2025/0008* (2013.01); *A61M 2025/0078* (2013.01); *A61M 2210/1078* (2013.01); *Y10T 29/49826* (2015.01)

(56) References Cited

U.S. PATENT DOCUMENTS

| | | | |
|---|---|---|---|
| 3,385,301 A | 5/1968 | Harautuneian | |
| 3,742,960 A | 7/1973 | Dye et al. | |
| 3,860,007 A | 1/1975 | Binard et al. | |
| 3,951,153 A | 4/1976 | Leucci | |
| 4,264,312 A | 4/1981 | Cianci | |
| 4,813,935 A | 3/1989 | Haber et al. | |
| 5,078,681 A | 1/1992 | Kawashima | |
| 5,100,385 A | 3/1992 | Bromander | |
| 5,391,148 A | 2/1995 | Bonis | |
| 5,429,620 A | 7/1995 | Davis | |
| 6,007,521 A | 12/1999 | Bidwell et al. | |
| 6,050,973 A | 4/2000 | Duffy | |
| 6,375,637 B1 | 4/2002 | Campbell et al. | |
| 6,575,932 B1 | 6/2003 | O'Brien et al. | |
| 6,749,583 B2 | 6/2004 | Briscoe et al. | |
| 8,287,447 B2 | 10/2012 | Gasche et al. | |
| 2002/0198558 A1 | 12/2002 | Briscoe et al. | |
| 2003/0163115 A1 | 8/2003 | Gershowitz | |
| 2005/0085891 A1* | 4/2005 | Goto | A61F 2/94 623/1.11 |
| 2006/0167438 A1 | 7/2006 | Kaiser et al. | |
| 2008/0009793 A1 | 1/2008 | Dabbs | |
| 2009/0171317 A1 | 7/2009 | Versi | |

\* cited by examiner

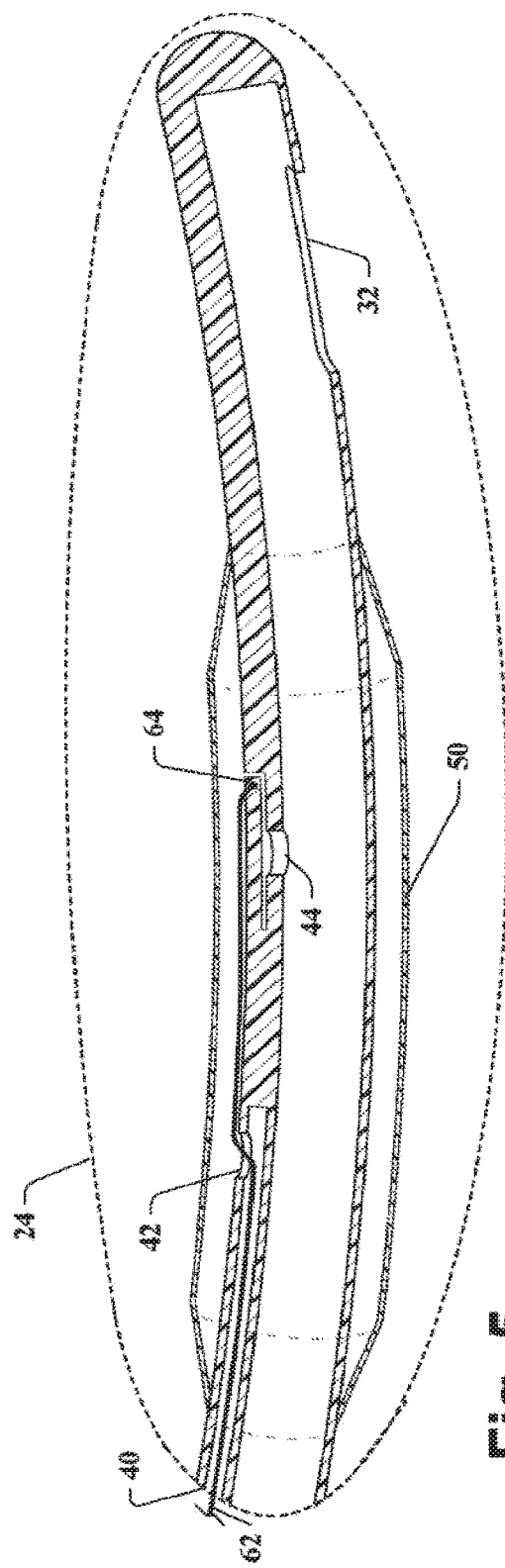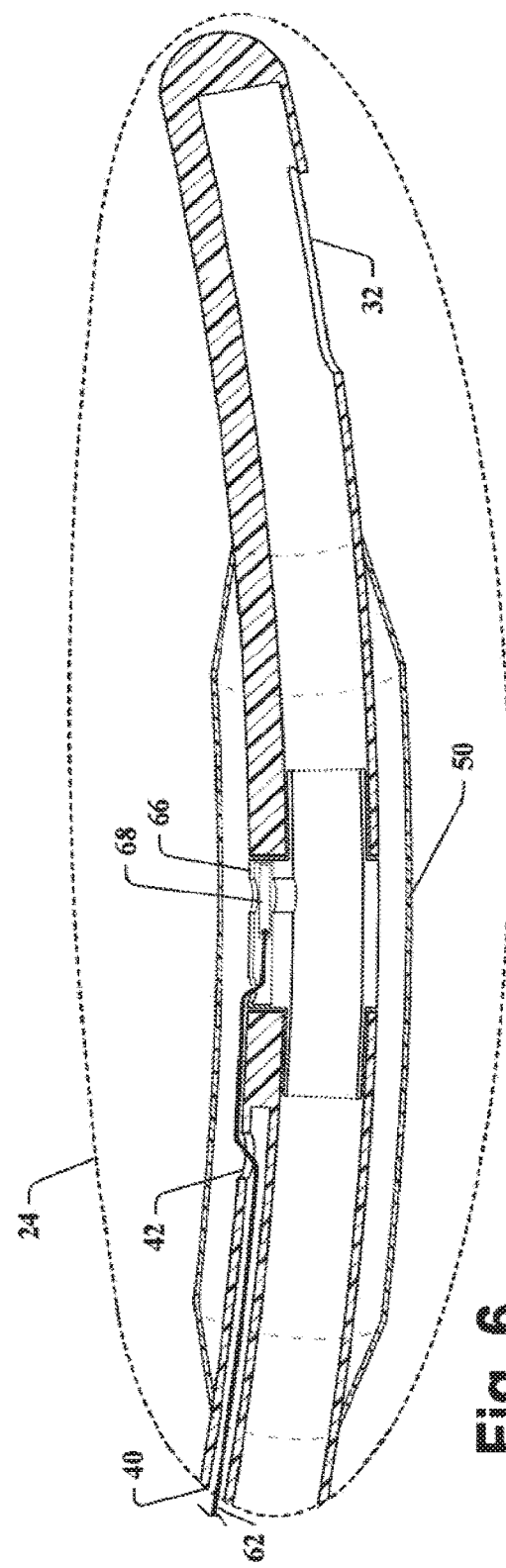

BALLOON CATHETER

CROSS REFERENCE TO RELATED APPLICATIONS

This application is continuation of U.S. application Ser. No. 14/987,464 filed Jan. 4, 2016, which is a continuation of U.S. application Ser. No. 13/943,971 filed Jul. 17, 2013 now U.S. Pat. No. 9,227,042 issued Jan. 5, 2016, which is a divisional of U.S. application Ser. No. 12/562,658 filed Sep. 18, 2009 now U.S. Pat. No. 8,500,684 issued Aug. 6, 2013, all of which are incorporated by reference herein in their entireties.

TECHNICAL FIELD

The subject disclosure relates to medical devices, and more particularly relates to balloon catheters that can be inserted into a vessel of a human body to perform medical procedures. The subject disclosure is particularly relevant to minimizing the damage caused to a human body when an inflated balloon catheter is removed from a vessel in the body.

BACKGROUND

By way of background concerning some conventional systems, balloon catheters, such as urinary catheters, can be used for a variety of medical procedures, including drainage of bodily fluids. Conventional urinary catheters, such as Foley catheters, can provide a channel for voiding fluid contained by the urinary bladder. Foley catheters are conventionally designed to be inserted into the urethral meatus and advanced through the urethra into the urinary bladder. They can contain a catheter tip with a balloon (e.g., retention balloon or anchor balloon), a fluid drainage lumen for draining urine from the urinary bladder, and a balloon inflation lumen for inflating or deflating the balloon. Conventionally, the portion of the Foley catheter including the catheter tip and balloon is advanced into the urinary bladder, at which point an inflation device can be used to insert fluid through the balloon inflation lumen and into the attached balloon, causing the balloon to inflate, securing the Foley catheter in place. In order to remove the Foley catheter from the bladder, fluid is conventionally withdrawn from the balloon through the balloon inflation lumen, causing the balloon to deflate. Once deflated, the Foley catheter can be retracted from the urinary bladder through the urethra, and removed from the human body.

However, the use of Foley catheters and other balloon catheters carries with it a variety of deficiencies. One such deficiency conventionally associated with the use of a Foley catheter is urethral injury resulting from removal of the Foley catheter with a fully- or partially-inflated balloon (e.g., inflated Foley catheter), such as when tension is applied to the portion of the Foley catheter outside the human body. With sufficient tension, the inflated Foley catheter balloon can be pulled through the urethra (e.g., traumatic Foley catheter removal), resulting in urethral injury, mucosal tears and lacerations, hematuria, or urethral disruption, and can lead to urethral strictures and scar formation causing subsequent urinary tract obstruction. Traumatic Foley catheter removal can also disrupt or damage the urethral sphincters which may lead to permanent urinary incontinence. Furthermore, removal of an inflated Foley catheter can result in significant penile injury in males and complete bladder eversion in women. The problem of traumatic Foley catheter removal is common, and is a frequent indication for urologic consultation. Traumatic Foley catheter removal is classically performed by patients having diminished mental capacity, including dementia or delirium, but can occur in any patient population. Unintentional removal can also occur as a result of tripping over or stepping on catheter tubing external to the body, or as a result of transferring patients from one location to another, as is common during surgery.

Another deficiency conventionally associated with the use of a Foley catheter is the potential for a non-deflating balloon, which complicates catheter removal. According to some reports, the deficiency of a non-deflating balloon has been observed in approximately eight to nine percent of latex Foley catheters. A non-deflating balloon can have a variety of causes, including defective valves in the balloon inflation lumen, solute crystal formation in the balloon inflation lumen, or kinking of the Foley catheter that compromises the balloon inflation lumen.

An even further deficiency conventionally associated with the use of a Foley catheter is tissue trauma caused by an increase in pressure about the balloon when an inflated balloon is translumenally or percutaneously ruptured in order to remove the catheter from the human body. This can lead to the problem of retained balloon fragments within the urethra or bladder, which can encourage infection and calculus formation (e.g., lithiasis), potentially resulting in partial or complete urinary obstruction and recurrent urinary tract infections.

The above-described deficiencies of today's Foley catheters and other balloon catheters are merely intended to provide an overview of some of the problems of conventional systems, and are not intended to be exhaustive. Other problems with the state of the art and corresponding benefits of some of the various non-limiting embodiments may become further apparent upon review of the following detailed description.

SUMMARY

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of this summary is to present some concepts related to some exemplary non-limiting embodiments in a simplified form as a prelude to the more detailed description of the various embodiments that follow.

A balloon catheter is provided that can be inserted through a vessel into a human body to perform medical procedures. The balloon catheter can include an elongated catheter shaft defining a fluid drainage lumen and a balloon inflation lumen. The catheter shaft can have a proximal end portion and a distal end portion. A port can be disposed at the distal end portion of the catheter shaft such that the port is in fluid communication with the fluid drainage lumen. A balloon can be disposed at the distal end portion of the catheter shaft such that the balloon is in fluid communication with the balloon inflation lumen. A tension activated release valve can be disposed between the balloon and the fluid drainage lumen, for releasing fluid from the balloon into the fluid drainage lumen when tension is applied to the catheter shaft.

These and other embodiments are described in more detail below.

BRIEF DESCRIPTION OF THE DRAWINGS

Various non-limiting embodiments are further described with reference to the accompanying drawings in which:

FIG. 5 is a schematic cross-sectional side view of the distal end portion of a balloon catheter according to an embodiment, having a tension activated flap release device;

FIG. 6 is a schematic cross-sectional side view of the distal end portion of a balloon catheter according to an embodiment, having a tension activated gate valve release device.

DETAILED DESCRIPTION

Overview

Figure 1:
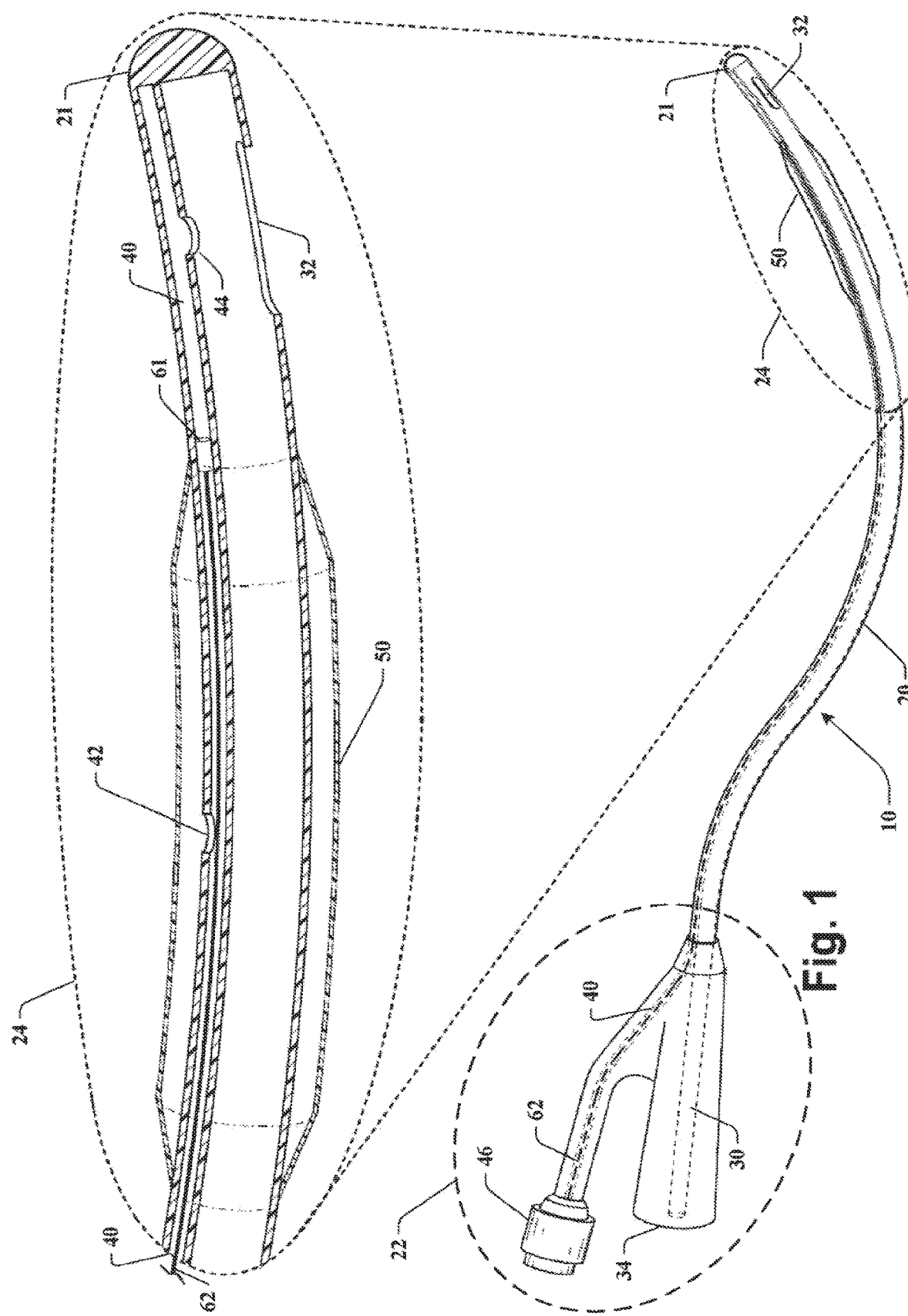
FIG. 1 is a schematic perspective view of a balloon catheter according to an embodiment with a deflated balloon, with a cross-sectional side view of the distal end portion.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, well-known structures and devices are shown in block diagram form in order to facilitate describing the claimed subject matter.

As used in this application, the terms "catheter," "balloon catheter," "urinary catheter," "Foley catheter" or the like can refer to a flexible tube inserted into the human body to introduce or withdraw fluids.

Moreover, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or." Therefore, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

As discussed in the background, among other things, current Foley catheters and other balloon catheters tend to cause urethral injury when removed in a fully- or partially-inflated state, tend to exhibit non-deflating balloons that complicate catheter removal, and tend to cause tissue trauma and retained foreign particles (e.g., balloon fragments) when an inflated balloon is ruptured in order to remove the catheter from a human body.

At least partly in consideration of these deficiencies of conventional Foley catheters and other balloon catheters, various embodiments of a balloon catheter are provided that provide a way for fluid contained by an inflated balloon of a balloon catheter to be released into a fluid drainage lumen out of the body, aiding in removal of the balloon catheter from a human body. As noted herein, various release devices can be employed to release fluid contained by an inflated balloon of a balloon catheter into a fluid drainage lumen out of the body.

Details of various other exemplary, non-limiting embodiments are provided below.

Balloon Catheter

The present invention describes an apparatus and method for deflating a balloon catheter apparatus. According to an exemplary embodiment, the balloon catheter includes a release device disposed between a balloon portion and a fluid drainage lumen of the balloon catheter. The release device allows the balloon catheter having an inflated balloon portion to be removed from a vessel in a human body without causing trauma to surrounding tissue, by releasing fluid from the balloon when longitudinal force (e.g., tension) is applied to the catheter shaft. When tension is applied to the portion of the balloon catheter outside the human body, the catheter shaft lengthens as the inflated balloon portion resists removal from the vessel in which it is positioned. When the shaft lengthens a predetermined amount, the release device is enabled to rapidly release fluid from the balloon portion into the fluid drainage lumen and out of the body. With fluid released from the balloon portion, the balloon portion deflates and the catheter can be safely removed without causing urethral injury. According to an exemplary embodiment, one end of a tether is attached to an activating member of the release device, while the other end of the tether is attached about the portion of the catheter shaft outside the human body. Tension applied to the relatively elastic catheter shaft causes the relatively inelastic tether to pull on the activating member of the release device, enabling the release device to rapidly release fluid from the balloon portion into the fluid drainage lumen and out of the body. In one particular embodiment, an open-ended (e.g., hollow ended) catheter tip can be employed for enabling urine to freely pass from the bladder into the catheter, in the event that the catheter is only partially withdrawn from the body, and the tip remains located within the urethra.

Referring now to the drawings, with reference initially to FIG. 1, a balloon catheter apparatus 10 according to an exemplary embodiment can include an elongated catheter shaft 20 defining a fluid drainage lumen 30 and a balloon inflation lumen 40. The catheter shaft 20 has a proximal end portion 22 about the proximal end and a distal end portion 24 about the distal end. A catheter tip 21 is disposed at the distal end of the catheter shaft 24. The catheter shaft 20 can be flexible to facilitate insertion and removal of the catheter shaft 20 from channels in a human body. In particular, the catheter shaft 20 can be flexible to follow the natural curvature of the urethra when the catheter shaft 20 is inserted through the urethral meatus and advanced through the urethra and into the urinary bladder. The catheter shaft 20 can be elastic (e.g., extendable), such that the length of the catheter shaft 20 can be extended by applying tension to one end of the catheter shaft 20 while the other end of the catheter shaft 20 remains substantially stationary (e.g., stretching the catheter shaft). According to an exemplary embodiment, the catheter shaft 20 may be extended when the distal end portion 24 is secured inside a vessel (e.g., secured by an inflated balloon), and tension (e.g., longitudinal force) is applied to the proximal end portion 22 of the catheter shaft 20, in a direction away from the distal end portion 24.

Figure 2:
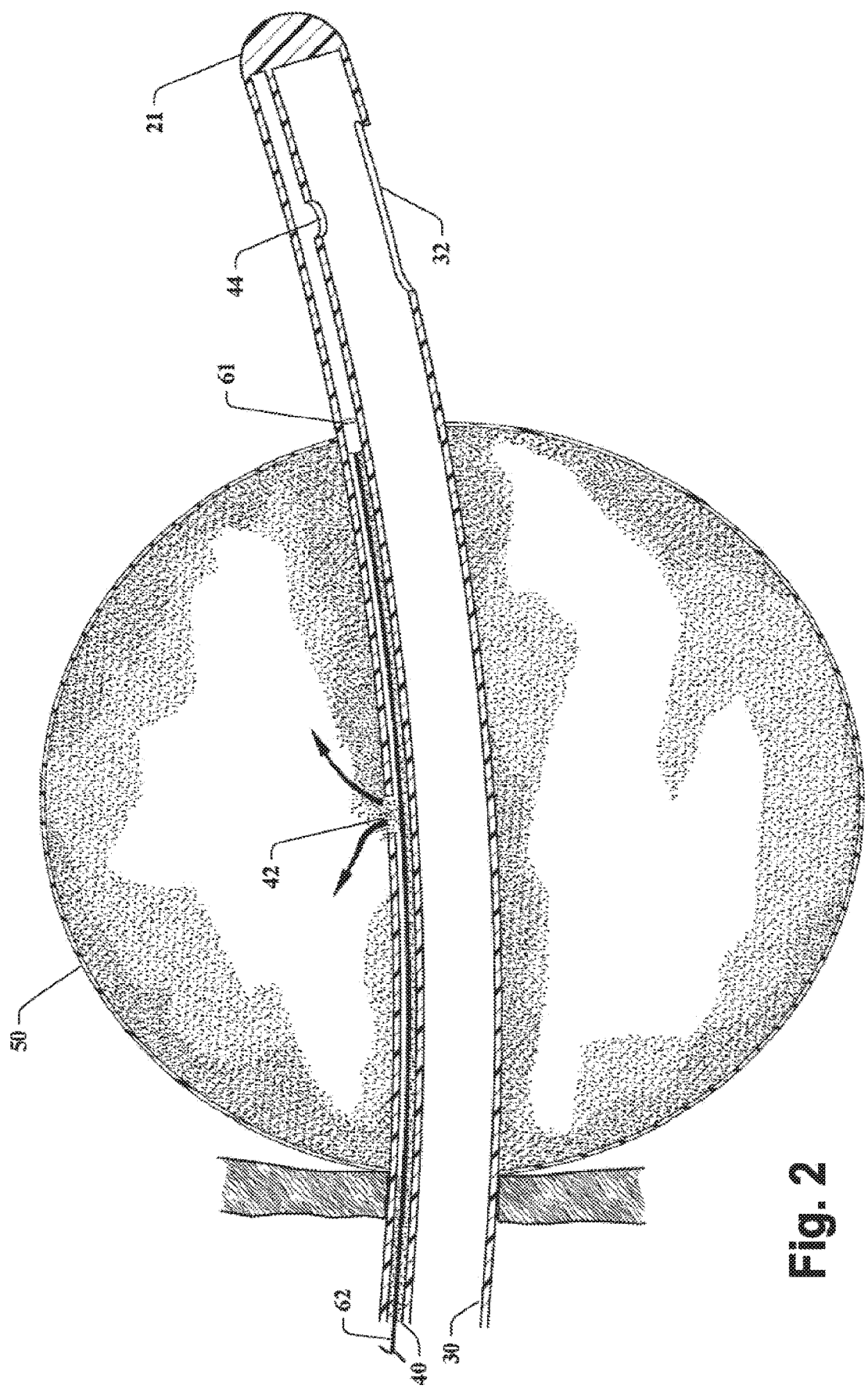
FIG. 2 is a schematic cross-sectional side view of a balloon catheter according to an embodiment inserted into a vessel, illustrating fluid passing through the balloon inflation lumen into the balloon, causing it to inflate.
Figure 3:
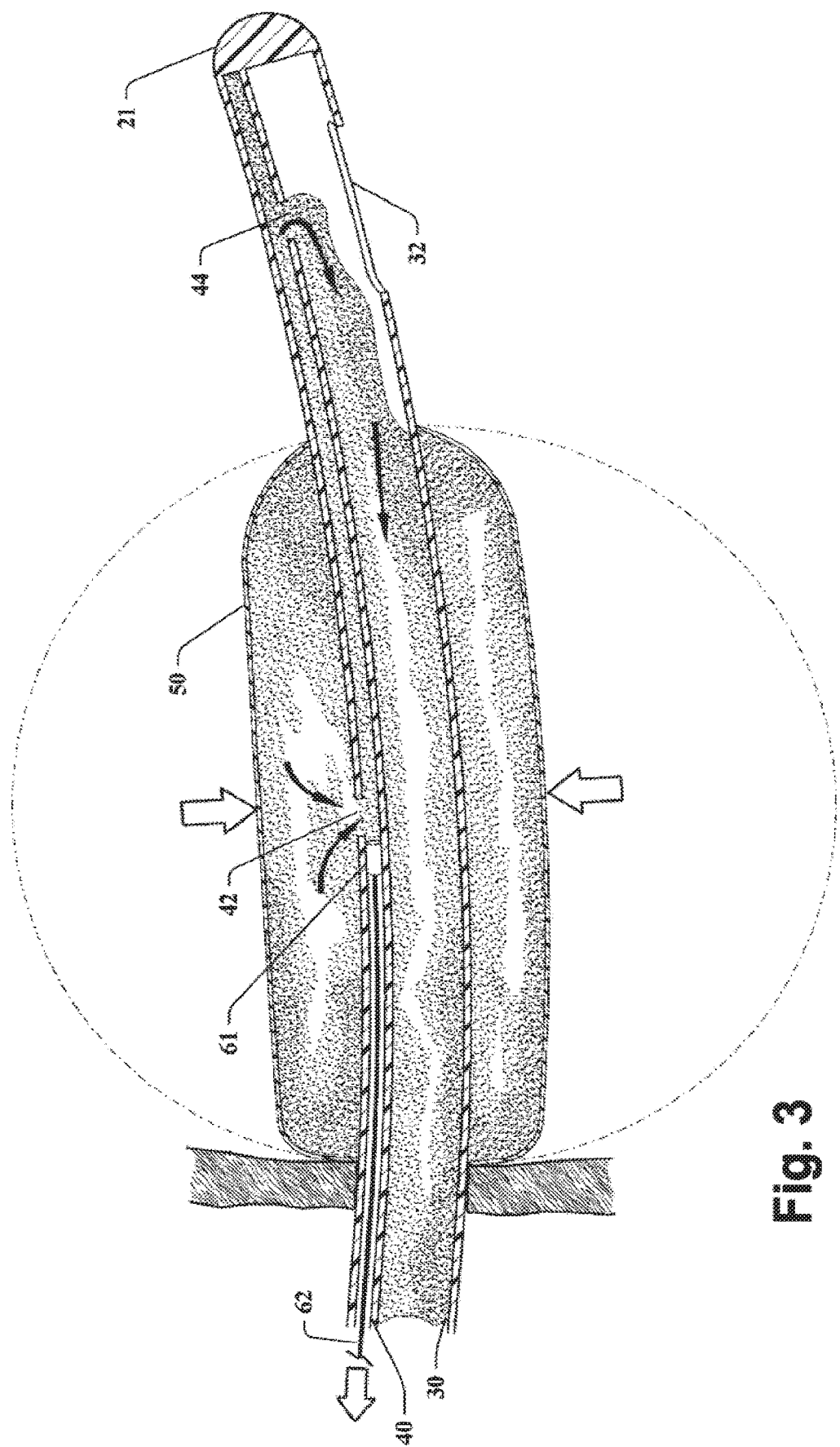
FIG. 3 is a schematic cross-sectional side view of a balloon catheter according to an embodiment inserted into a vessel, illustrating fluid passing from the balloon through a tension activated release valve and into a fluid drainage lumen, causing the balloon to deflate.

According to an exemplary embodiment, the distal end portion 24 can include a fluid drainage port 32 in fluid communication with the fluid drainage lumen 30. As shown in FIGS. 2 and 3, the catheter shaft 20 can be inserted into a vessel (e.g., the urinary bladder) so that the fluid drainage port 32 is in fluid communication with the vessel. Fluid (e.g., urine) in the vessel can travel through the fluid drainage port 32, into the fluid drainage lumen 30, and out of the body. The proximal end portion 22 of the catheter shaft 20 may have a drainage connector 34 in fluid communication with the fluid drainage lumen 30. The drainage connector 34 can be used to direct fluid from the fluid drainage lumen 30 into a collection or disposal apparatus, such as a urine storage bag.

As shown in FIG. 1, a balloon inflation port 42 can be disposed about the distal end portion 24 of the catheter shaft 20 according to an embodiment, such that the balloon inflation port 42 is in fluid communication with the balloon inflation lumen 40. The balloon inflation port 42 can be positioned in a spaced apart configuration from the fluid drainage port 32.

A balloon portion 50 can be disposed about the distal end portion 24 of the shaft, such that the balloon portion 50 is in fluid communication with the balloon inflation port 42. In one exemplary embodiment, the balloon portion 50 can be disposed between the fluid drainage port 32 and the proximal end portion 22 of the shaft. The balloon portion 50 can be constructed from a deformable or elastic membrane (e.g., latex, silicone) that surrounds a longitudinal section of the catheter shaft 20. The balloon portion 50 can also be sealed to a longitudinal section of the catheter shaft 20, so that fluid can be contained between the balloon portion 50 and the catheter shaft 20. The balloon portion 50 can be radially inflated in response to positive pressure of fluid communicated into the balloon portion 50 through the balloon inflation lumen 40.

The proximal end portion 22 of the catheter shaft 20 may include a balloon inflation connector 46 in fluid communication with the balloon inflation lumen 40. The balloon inflation connector 46 can be connected to a balloon inflation device. The balloon inflation device can be used to inflate or deflate the balloon portion 50. In an exemplary embodiment, the balloon inflation device can be a piston pump, such as a syringe. When the balloon inflation device is connected to the balloon inflation connector, fluid (e.g., air, saline) expelled from the balloon inflation device travels through the balloon inflation lumen 40 and into the balloon portion 50, causing the balloon portion 50 to inflate. In an exemplary embodiment, a valve may be placed in the balloon inflation connector 46 or in the balloon inflation lumen 40 to prevent the release of fluid back through the balloon inflation connector 46 when the balloon inflation device is removed from the balloon inflation connector 46. In order to deflate the balloon portion 50, a balloon inflation device can be attached to the balloon inflation connector 46, and fluid from the balloon portion 50 can be drawn into the balloon inflation device through the balloon inflation lumen 40, causing the balloon portion 50 to deflate.

Figure 4:
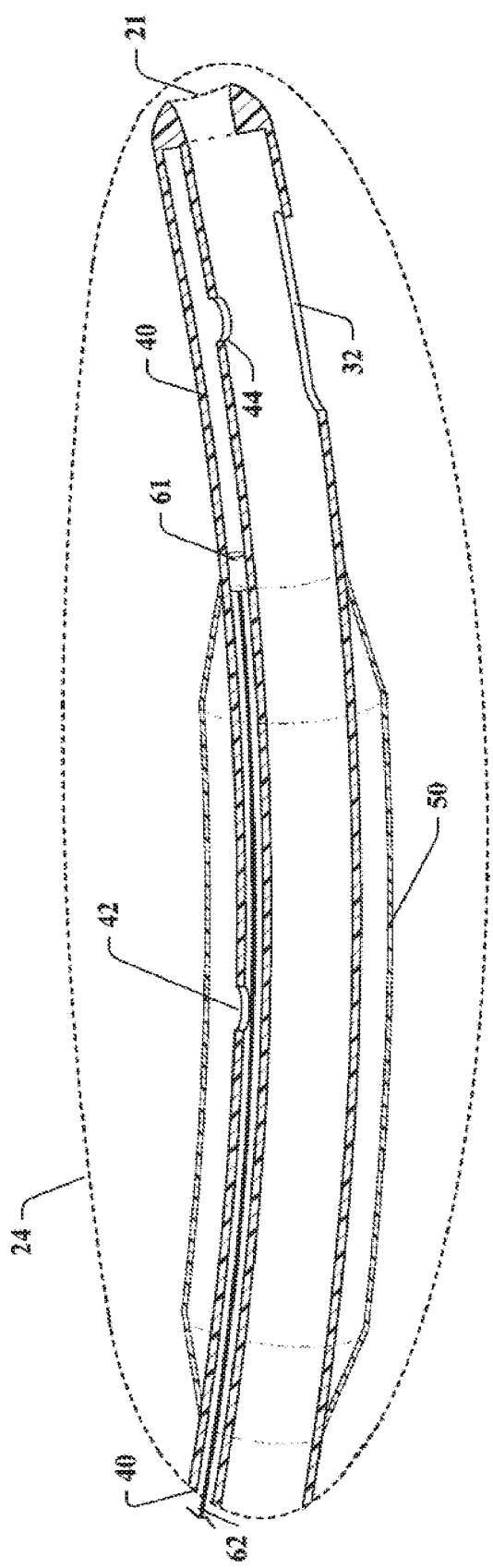
FIG. 4 is a schematic cross-sectional side view of the distal end portion of a balloon catheter according to an embodiment, having an open-ended catheter tip.
Figure 7:
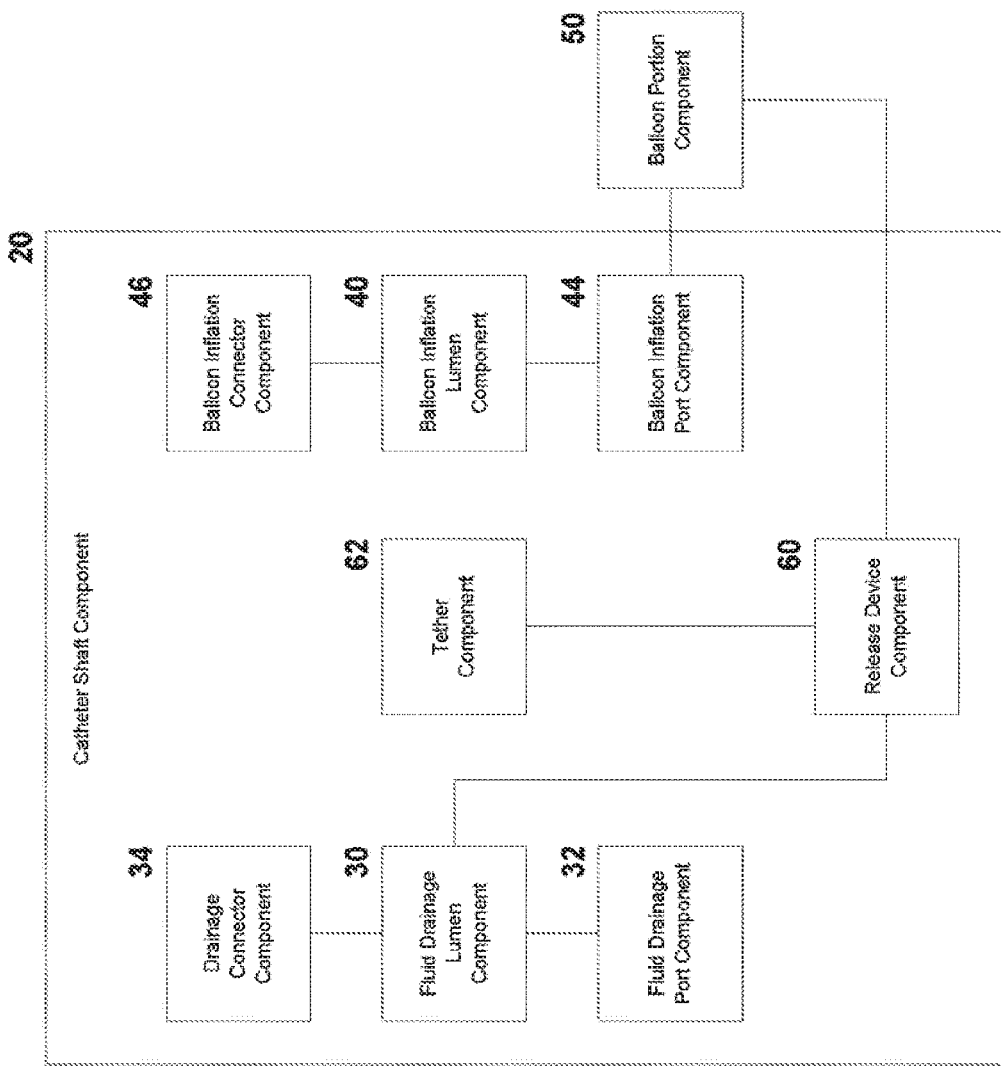
FIG. 7 is a schematic system block diagram of a balloon catheter according to an embodiment.

According to an exemplary embodiment, a pressure release port 44 can be disposed at the distal end portion 24 of the catheter shaft 20, between the balloon inflation lumen 40 and the fluid drainage lumen 30, such that the pressure release port 44 places the balloon inflation lumen 40 in fluid communication with the fluid drainage lumen 30. The pressure release port 44 can be disposed longitudinally along the balloon inflation lumen 40 between the balloon inflation port 42 and the catheter tip 21. In an exemplary embodiment, the catheter tip 21 can be open-ended (e.g., hollow), as shown in FIG. 4. The catheter tip 21 can be open to the fluid drainage port 32, such that fluid can pass through the fluid drainage port 32 in the catheter tip 21 and into the fluid drainage lumen 30. Moreover, it should be appreciated that the pressure release port 44 can be located between the balloon inflation lumen 40 and the fluid drainage lumen 30 at any location between the balloon inflation port 42 and the distal end of the catheter shaft 20. In one exemplary embodiment, the pressure release port 44 can be located at the distal end of the catheter shaft 20, such that the pressure release port 44 is a notch between the balloon inflation lumen 40 and the fluid drainage lumen 30.

As shown in FIGS. 1 through 7, a release device 60 can be disposed between the balloon portion 50 and the fluid drainage lumen 30, for selectively releasing fluid from the balloon portion 50 into the fluid drainage lumen 30, and out of the body. The release device 60 can comprise an activating member, for enabling fluid flow through the release device. A substantially non-elastic (e.g., substantially non-extendable) tether 62 can be affixed to the activating member, for manipulating the position of the activating member to activate the release device 60. According to an exemplary embodiment shown in FIGS. 1 through 4, the activating member can comprise a plug 61 within the balloon inflation lumen 40, positioned between the balloon inflation port 42 and the catheter tip 21. The substantially non-elastic tether 62 can be affixed to the plug 61 and extend through the balloon inflation lumen 40 toward the proximal end portion of the catheter shaft 22. In a disabled state, the plug 61 substantially seals the balloon inflation lumen 40 so that fluid within the balloon inflation lumen 40 on one side of the plug 61 is unable to flow past the plug 61 and through the balloon inflation lumen 40 to the pressure release port 44. It should be understood that the release device 60 could include any device having an activating member (e.g., valve, flap) suitable for controlling the flow of a liquid.

According to an exemplary embodiment as shown in FIG. 5, the release device 60 can comprise a pressure release port 44 covered by a flexible flap 64 that serves as an activating member, for placing the balloon portion 50 in fluid communication with the fluid drainage lumen 30 when the flap 64 is pulled away from the pressure release port 44. A substantially non-elastic tether 62 can be affixed to the activating member (e.g., the flap 64) and extend through the balloon inflation lumen 40 in a direction toward the proximal end portion of the catheter shaft 22. In a disabled state, the flap 64 prevents fluid in the balloon portion 50 from flowing past the flap 64, through the pressure release port 44 and into the fluid drainage lumen 30. In an enabling position, the tether has pulled on the flap 64, causing the flap 64 to lift and enable fluid from the balloon portion 50 to flow through the pressure release port 44, into the fluid drainage lumen 30 and out of the body. It should be understood that the flap 64 may be formed from a portion of the catheter shaft, such that the flap 64 has a weakened perimeter. According to an embodiment, tension applied to the flap 64 by the attached tether 62 causes the perimeter of the flap 64 to tear loose from the catheter shaft 20, exposing the pressure release port 44 and enabling fluid flow from the balloon portion 50 into the fluid drainage lumen 30.

As shown in FIG. 6, according to an exemplary embodiment, the release device 60 can comprise a valve 66 (e.g., sliding action valve, gate valve) between the balloon portion 50 and the fluid drainage lumen 30. The activating member may comprise the gate portion 68 of the valve 66. A substantially non-elastic tether 62 can be affixed to the gate portion 68, and extend through the balloon inflation lumen 40 in a direction toward the proximal end portion of the catheter shaft 22. In a disabled state, the valve 66 prevents fluid in the balloon portion 50 from flowing past the valve 66 into the fluid drainage lumen 30. In an enabling position, the valve 66 is opened (e.g., the gate is pulled back by the tether 62), enabling fluid from the balloon portion 50 to flow into the fluid drainage lumen 30 and out of the body.

According to an exemplary embodiment, the tether 62 has a proximal end and a distal end, wherein the proximal end is affixed to the balloon inflation lumen 40 about the proximal end portion 22 of the catheter shaft 20 and the distal end of the tether is affixed to the activating member of the release device 60, according to an embodiment. The proximal end of the tether 62 can be affixed to the balloon inflation lumen 40 about the balloon inflation connector 46. The proximal end of the tether 62 can also be affixed to a lever or switch, such that manipulation of the lever or switch imparts longitudinal movement of the tether within the balloon inflation lumen 40. It should be understood that the diameter of the tether 62 is less than the diameter of the balloon inflation lumen 40 so that fluid is able to pass through the balloon inflation lumen 40 with the tether 62 extending within. According to an exemplary embodiment, the tether 62 can comprise a semi-rigid structure that tends to prevent the balloon inflation lumen from kinking or otherwise becoming blocked.

FIGS. 2 and 3 illustrate how a balloon catheter apparatus 10 having an inflated balloon portion can be removed from a vessel in a human body, according to an embodiment. As shown in FIG. 2, the release device 60 of a deflated balloon catheter is initially disabled, preventing fluid flow from the balloon portion 50 through the pressure release port 44. The tether 62 maintains the activating member (e.g. plug 61) of the release device 60 so that the release device is in this disabling position as the balloon catheter apparatus 10 is inserted into a vessel and the balloon portion 50 is inflated. With the release device 60 in the disabling position, fluid inserted into the balloon inflation lumen 40 flows through the balloon inflation port 42 into the balloon portion 50, inflating the balloon portion 50.

As shown in FIG. 3, the activating member is manipulated so that the release device 60 is enabled (e.g., the plug 61 is advanced within the balloon inflation lumen 40 past the pressure release port 42, toward the proximal end portion 22 of the catheter shaft 22), enabling fluid flow from the balloon portion 50 through the pressure release port 44. In the enabling position, pressurized fluid from the balloon portion 50 flows through balloon inflation port 42 into the balloon inflation lumen 40, through the pressure release port 44, and into the fluid drainage lumen 30, deflating the balloon portion 50. The release device 60 can be enabled by applying longitudinal force (e.g., tension) to the tether, in the direction away from the catheter tip 21 (e.g., toward the proximal end portion 22 of the catheter shaft).

According to an exemplary embodiment, a balloon catheter apparatus 10 is secured in a vessel of a human body by an inflated balloon portion 50. When an attempt is made to withdraw the catheter shaft 20 from vessel by applying tension to the proximal end portion 22 of the catheter shaft 20, the inflated balloon portion 50 prevents removal of the distal end portion 24 of the catheter shaft from the vessel, and the catheter shaft 20 stretches (e.g., lengthens). As the catheter shaft 20 lengthens, the substantially non-elastic tether 62, the proximal end of which is secured to the proximal end portion 22 of the catheter shaft 20, advances the plug 61 from its disabling position to its enabling position. Once the plug 61 is in its enabling position, pressurized fluid from the balloon portion 50 flows into the fluid drainage lumen 40, deflating the balloon portion 50, and allowing withdrawal of the catheter shaft 20 while minimizing tissue damage caused by the balloon portion 50.

Method of Deflating a Balloon Catheter

While still referring to FIGS. 1 through 7, a method of balloon catheterization can include the act of employing a tether to activate a release device to deflate a balloon catheter.

A method of deflating a balloon catheter apparatus 10 of the type described supra can, according to an embodiment, include the acts of providing a balloon catheter apparatus 10 with an inflated balloon portion 50, advancing the tether 62 toward the proximal end portion 22 of the catheter shaft 20 to active the release device 60, enabling fluid flow from the inflated balloon portion 50 into the fluid drainage lumen 30 and out of the body, thereby deflating the balloon.

According to an embodiment, a method of deflating a balloon catheter apparatus 10 of the type described supra, includes the acts of providing a balloon catheter having an inflated balloon portion, and extending the catheter shaft, thereby advancing the tether toward the proximal end of the catheter shaft to active the release device, enabling fluid flow from the inflated balloon portion 50 into the fluid drainage lumen 30.

The word "exemplary" is used herein to mean serving as an example, instance, or illustration. For the avoidance of doubt, the subject matter disclosed herein is not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

In view of the exemplary apparatus and methods described supra, methodologies that may be implemented in accordance with the disclosed subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter.

While the various embodiments have been described in connection with the preferred embodiments of the various figures, it is to be understood that other similar embodiments may be used or modifications and additions may be made to the described embodiment for performing the same function without deviating therefrom. Therefore, the present invention should not be limited to any single embodiment, but rather should be construed in breadth and scope in accordance with the appended claims.

We claim:

1. A balloon catheter comprising: an elongated catheter shaft defining a fluid drainage lumen and a balloon inflation lumen, the catheter shaft having a proximal end and a distal end; a fluid drainage port disposed about the distal end of the catheter shaft, the fluid drainage port in fluid communication with the fluid drainage lumen; a balloon inflation port disposed about the distal end of the catheter shaft, the balloon inflation port in fluid communication with the balloon inflation lumen; a balloon portion disposed about the distal end of the catheter shaft, the balloon portion in fluid communication with the balloon inflation port; a release device in fluid communication with the balloon portion and the fluid drainage lumen, the release device comprising an activating member; and a tether having a proximal end and a distal end, the distal end of the tether attached to the activating member of the release device; wherein the release device further comprises a pressure release port in fluid communication with the fluid drainage lumen and the balloon inflation lumen, the pressure release port disposed between the balloon inflation port and the distal end of the catheter shaft, the activating member comprising a slidable plug disposed within the balloon inflation lumen, the slidable plug being disposed between the balloon inflation port and the pressure release port.

2. A balloon catheter according to claim 1, wherein the plug seals the balloon inflation lumen.

3. A balloon catheter according to claim 1, wherein the elongated catheter shaft being elastic.

4. A balloon catheter according to claim 1, wherein the tether being substantially non-elastic.

5. A balloon catheter according to claim 1, wherein the tether being disposed within the balloon inflation lumen.

6. A balloon catheter according to claim 1, wherein the proximal end of the tether being attached proximal to the distal end of the catheter shaft.

7. A balloon catheter according to claim 1, wherein the distal end of the catheter shaft is open-ended.

8. A balloon catheter comprising: an elongated catheter shaft, the shaft being flexible, the shaft being elastic, the shaft defining a fluid drainage lumen and a balloon inflation lumen, the shaft having a distal end portion and a proximal end portion, the distal end portion comprising a fluid drainage port in fluid communication with the fluid drainage lumen, the proximal end portion comprising a connector configured to engage an inflation device, the proximal end portion comprising a connector to engage a device for draining fluid from the fluid drainage lumen, the shaft comprising: a balloon inflation port in fluid communication with the balloon inflation lumen, the balloon inflation port disposed about the distal end of the shaft, the balloon inflation port positioned in a spaced apart configuration from the fluid drainage port; a balloon portion disposed at the distal end portion of the shaft, the balloon portion between the fluid drainage port and the proximal end of the shaft, the balloon portion in fluid communication with the balloon inflation lumen, the balloon portion comprising: an elastic membrane surrounding a longitudinal section of the shaft, the membrane being radially inflatable in response to positive pressure of fluid communicated through the balloon inflation lumen; a pressure release mechanism for enabling fluid flow from the balloon into the fluid drainage lumen, the pressure release mechanism comprising: a pressure release port in the balloon inflation lumen, the pressure release port disposed between the balloon inflation port and the distal end portion of the shaft, the pressure release port for placing the balloon inflation lumen in fluid communication with the fluid drainage lumen; and a pressure release valve disposed between the balloon inflation port and the pressure release port, the pressure release valve configured to enable fluid flow from the balloon inflation port through the pressure release port, the pressure release valve comprising: a plug disposed within the balloon inflation lumen, the plug sealing the balloon inflation lumen, the plug capable of being advanced toward the proximal end portion; and a tether extending between the proximal end portion and the plug, the tether disposed within the balloon inflation lumen, the tether being substantially non-elastic, the tether having a first end and a second end, the first end being affixed to the proximal end portion and the second end being affixed to the plug.

* * * * *